(12) United States Patent
Simonnet et al.

(10) Patent No.: US 6,379,683 B1
(45) Date of Patent: Apr. 30, 2002

(54) NANOCAPSULES BASED ON DENDRITIC POLYMERS

(75) Inventors: Jean-Thierry Simonnet; Pascal Richart, both of Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/507,925

(22) Filed: Feb. 22, 2000

(30) Foreign Application Priority Data

Mar. 2, 1999 (FR) ............................................. 99 02579

(51) Int. Cl.[7] ......................... A61K 7/00; A61K 31/045
(52) U.S. Cl. .................... 424/401; 528/271; 514/788.1; 514/772.6; 514/975; 514/963; 514/725
(58) Field of Search ................................. 424/401, 486; 514/788.1, 772.6, 975, 963; 528/271

(56) References Cited

U.S. PATENT DOCUMENTS

| | | | |
|---|---|---|---|
| 5,338,532 A | * | 8/1994 | Tomalia et al. ............. 424/1.49 |
| 5,411,744 A | * | 5/1995 | Hill et al. .................... 424/450 |
| 6,114,458 A | * | 9/2000 | Hawker et al. .............. 525/242 |
| 6,162,448 A | * | 12/2000 | Nguyen et al. ............. 424/401 |

FOREIGN PATENT DOCUMENTS

| | | |
|---|---|---|
| EP | 0 254 447 | 1/1988 |
| EP | 0 274 961 | 7/1988 |
| EP | 0 447 318 A1 | 9/1991 |
| FR | 2 681 248 | 3/1993 |
| WO | WO 93/17060 | 9/1993 |
| WO | WO 96/12754 | 5/1996 |

OTHER PUBLICATIONS

Derwent (Database WPI), Mar. 16, 1989; AN 89–126027: JP 01071823A (Rhoto Pharm Co Ltd).

* cited by examiner

Primary Examiner—Diana Dudash
Assistant Examiner—Gina Yu
(74) Attorney, Agent, or Firm—Nixon & Vanderhye P.C.

(57) ABSTRACT

The present invention relates to nanocapsules consisting
of a lipid core forming or containing a lipophilic active principle, and
of a water-insoluble continuous envelope comprising at least one dendritic polymer of polyester type containing optionally modified terminal hydroxyl functions,
and to cosmetic and/or dermatological compositions containing the said nanocapsules based on dendritic polymers.

26 Claims, No Drawings

NANOCAPSULES BASED ON DENDRITIC POLYMERS

The present invention relates to nanocapsules based on dendritic polymers and to cosmetic and/or dermatological compositions containing them.

The encapsulation or absorption of lipophilic active principles in particles of submicron size has been known for several years and is widely used in particular in cosmetology and dermatology, since these particles, known as nanoparticles, are capable of crossing the superficial layers of the stratum corneum and of penetrating into the upper layers of the live epidermis to release the active principle therein. This penetration into deeper layers broadens the space of action of the active principles and obscures them from rapid removal by simple rubbing.

The term "nanoparticles" primarily encompasses two different systems: "nanospheres" consisting of a porous polymer matrix in which the active principle is absorbed and/or adsorbed, and "nanocapsules" with a structure of core-envelope type, i.e. a structure consisting of a lipid core forming or containing the active principle, this core being encapsulated in a water-insoluble continuous protective envelope. The present invention relates solely to this second vesicular type of nanoparticle, i.e. nanocapsules with a lipid core surrounded by a polymer membrane.

The encapsulation of active principles in capsules of submicron size makes it possible, admittedly, to convey the active molecules more deeply into the skin, but it does not always afford—contrary to what this "protective" structure might lead one to think—sufficient stability of the active principle with respect to the surrounding physicochemical conditions.

The problem of the instability of the active principle arises in particular for substances that are sensitive to oxidation, light, high temperatures and/or acidic or basic pHs. Such a substance which is very commonly used in cosmetics is, for example, retinol (vitamin $A_1$), which is sensitive to oxidation, in particular at acidic pH.

One approach for stabilizing retinol consists in adding lipophilic antioxidants and chelating agents to compositions containing it and in adjusting the pH of these compositions to a value of between 5 and 10 (WO 96/31194).

The Applicant has now discovered that encapsulation in nanocapsules based on a specific type of polymer significantly improves the stability of retinol, and does so in particular in the absence of antioxidants and at pH values below 5.

The polymers which allow such a favourable effect to be obtained are known as dendritic polymers. These polymers have a structure of hyperbranch polyester type which will be described in greater detail hereinbelow.

Thus, the encapsulation of retinol in nanocapsules with an envelope formed from dendritic polymers of the type described above gives this active molecule satisfactory stability, i.e. a loss of activity of less than 20% after storage for 1 month at 45° C., whereas, under equivalent conditions, this same molecule encapsulated in other polymers commonly used for nanoencapsulation (for example polycaprolactone or cellulose derivatives) shows a loss of activity at least equal to 30% and possibly being as much as 100%.

One subject of the invention is thus nanocapsules consisting
- of a lipid core forming or containing a lipophilic active principle, and
- of a water-insoluble continuous envelope comprising at least one dendritic polymer of polyester type containing terminal hydroxyl functions.

A subject of the invention is also cosmetic and/or dermatological compositions containing the said nanocapsules based on dendritic polymers.

Another subject of the invention is a process for preparing nanocapsules based on the above dendritic polymers.

Other subjects will become apparent on reading the description and the examples which follow.

Dendritic polymers or dendrimers (from the Greek dendron=tree) are "arborescent" polymer molecules, i.e. highly branched polymers, which were invented by D. A. Tomalia and his team at the start of the 1990s (Donald A. Tomalia et al., *Angewandte Chemie, Int. Engl. Ed.*, vol. 29, No. 2, pages 138–175). They are molecular structures constructed around a central unit which is generally multivalent. Linked around this central unit, in concentric layers and according to a fully defined structure, are branched chain-extending units thus giving rise to monodisperse symmetrical macromolecules of well-defined chemical structure and stereochemistry.

The dendritic polymers constituting the envelope of the nanocapsules of the present invention are hyperbranched polymers with the chemical structure of a polyester and which are terminated with hydroxyl groups optionally modified with at least one chain-terminating agent. The structure and preparation of such polymers is described in patent applications WO-A-93/17060 and WO 96/12754.

More specifically, the dendritic polymers used in the compositions of the present invention can be defined as being highly branched macromolecules of polyester type, consisting
- of a central unit derived from an initiator compound bearing one or more hydroxyl functions (a),
- of chain-extending units derived from a chain-extending molecule bearing a carboxyl function (b) and at least two hydroxyl functions (c), each of the hydroxyl functions (a) of the central molecule being the starting point of a polycondensation reaction (by esterification) which starts with the reaction of the hydroxyl functions (a) of the central molecule with the carboxyl functions (b) of the chain-extending molecules, and then continues by reaction of the carboxyl functions (b) with the hydroxyl functions (c) of the chain-extending molecules.

A "generation X" dendrimer refers to a hyperbranched polymer prepared by X condensation cycles, each cycle consisting in reacting all of the reactive functions of the central unit or of the polymer with one equivalent of a chain-extending molecule.

The initiator compound bearing one or more hydroxyl functions and forming the central unit around which the dendritic structure will be constructed is a monohydroxy, dihydroxy or polyhydroxy compound. It is generally chosen from
- (a) a monofunctional alcohol,
- (b) an aliphatic, cycloaliphatic or aromatic diol,
- (c) a triol,
- (d) a tetrol,
- (e) a sugar alcohol,
- (f) anhydro-ennea-heptitol or dipentaerythritol,
- (g) an α-alkylglycoside,
- (h) a polyalkoxy polymer obtained by polyalkoxylation of one of the alcohols (a) to (g), with a molar mass of not more than 8000.

As examples of preferred initiator compounds for preparing the dendritic polymers used in the present invention, mention may be made of ditrimethylolpropane, ditrimethylolethane, dipentaerythritol, pentaerythritol, an alkoxylated pentaerythritol, trimethylolethane, trimethylolpropane, an alkoxylated trimethylolpropane, glycerol, neopentyl glycol, dimethylolpropane or 1,3-dioxane-5,5-dimethanol.

These hydroxylated initiator compounds forming the central unit of the future dendrimer are reacted with molecules referred to as chain-extending molecules, which are compounds of monoacidic diol type chosen from monocarboxylic acids comprising at least two hydroxyl functions, and monocarboxylic acids comprising at least two hydroxyl functions, one or more of which bear(s) a hydroxyalkyl substituent.

Preferred examples of such compounds are dimethylolpropionic acid, α,α-bis(hydroxymethyl)butyric acid, α,α,α-tris(hydroxymethyl)acetic acid, α, α-bis(hydroxymethyl) valeric acid, α,α-bis(hydroxy)-propionic acid and 3,5-dihydroxybenzoic acid.

According to one particularly preferred embodiment of the present invention, the initiator compound is chosen from trimethylolpropane, pentaerythritol and an ethoxylated pentaerythritol, and the chain-extending molecule is dimethylolpropionic acid.

Some of the terminal hydroxyl functions of the dendritic polymers of polyester type used in the nanocapsules of the present invention can bear substituents derived from at least one chain-terminating agent.

The fraction of these terminal hydroxyl functions bearing a chain-terminating unit is generally between 1 and 90 mol %, preferably between 10 and 50 mol %, relative to the total number of terminal hydroxyl functions.

The choice of a suitable chain-terminating agent makes it possible to modify as desired the physicochemical properties of the dendritic polyesters used in the compositions of the present invention.

The said chain-terminating agent can be chosen from a wide variety of compounds capable of forming covalent bonds with the terminal hydroxyl functions.

These compounds encompass, in particular:

i) saturated or unsaturated, aliphatic or cycloaliphatic monocarboxylic acids (or anhydrides), ii) saturated or unsaturated fatty acids, iii) aromatic monocarboxylic acids, iv) diisocyanate monomers or oligomers or addition products thereof, v) epihalohydrins, vi) glycidyl esters of a monocarboxylic acid or of a $C_{1-24}$ fatty acid, vii) glycidyl ethers of $C_{1-24}$ monovalent alcohols, viii) addition products derived from a saturated or unsaturated, aliphatic or cycloaliphatic mono-, di- or polycarboxylic acid, or from the corresponding anhydrides, ix) addition products derived from an aromatic mono-, di- or polycarboxylic acid or from the corresponding anhydrides, x) epoxides of an unsaturated $C_{3-24}$ monocarboxylic acid or of a corresponding triglyceride, xi) saturated or unsaturated, aliphatic or cycloaliphatic monofunctional alcohols, xii) aromatic monofunctional alcohols, xiii) addition products derived from a saturated or unsaturated, aliphatic or cycloaliphatic mono-, di- or polyfunctional alcohol, and xiv) addition products derived from an aromatic mono-, di- or polyfunctional alcohol.

Examples of chain-terminating agents which may be mentioned are lauric acid, linseed fatty acids, soybean fatty acids, tallow fatty acids, dehydrogenated castor oil fatty acids, crotonic acid, capric acid, caprylic acid, acrylic acid, methacrylic acid, benzoic acid, para-tert-butylbenzoic acid, abietic acid, sorbinic acid, 1-chloro-2,3-epoxypropane, 1,4-dichloro-2,3-epoxybutane, epoxidized soybean fatty acids, trimethylolpropane diallyl ether maleate, 5-methyl-1,3-dioxane-5-methanol, 5-ethyl-1,3-dioxane-5-methanol, trimethylolpropane diallyl ether, pentaerythrityl triallyl ether, pentaerythrityl triacrylate, triethoxylated pentaerythrityl triacrylate, toluene 2,4-diisocyanate, toluene 2,6-diisocyanate, hexamethylene diisocyanate or isophorone diisocyanate.

Among the chain-terminating agents which are particularly preferred are capric acid and caprylic acid or a mixture thereof.

The dendritic polymers of polyester type containing terminal hydroxyl functions and optionally bearing chain-terminating groups are known and are sold by the company Perstorp.

Among the polymers which it is particularly preferred to use in the present invention are a dendritic polyester obtained by polycondensation of dimethylolpropionic acid with trimethylolpropane and which is free of chain-terminating agents, for example the product sold under the name "Boltorn® H40 (TMP core)" by the company Perstorp;

a dendritic polyester obtained by polycondensation of dimethylolpropionic acid with polyoxyethylenated pentaerythritol (on average 5 units of ethylene oxide to each hydroxyl function), which is free of a chain-terminating agent, for example the product sold under the name "Boltorn® H30" by the company Perstorp;

a generation 3 dendritic polyester obtained by polycondensation of dimethylolpropionic acid with polyoxyethylenated pentaerythritol (on average 5 units of ethylene oxide to each hydroxyl function), 50% of the hydroxyl functions of which are esterified with $C_{8-10}$ acids and in particular capric($C_{10}$) acid and caprylic ($C_8$) acid ("Boltorn® H30 (esterified)" sold by the company Perstorp).

Among these three polymers, the last one is the one most particularly preferred.

These dendritic polymers are used to prepare nanocapsules consisting of a lipid core forming or containing an active principle surrounded by an envelope formed by these polymers.

The process for preparing nanocapsules which is used by the Applicant Company is preferably the one described in EP-A-0 274 961. It comprises the steps consisting in dissolving the polymer, the lipid phase forming or containing the active principle and optionally a surfactant acting as a coating agent, in a suitable organic solvent, i.e. a solvent which is miscible with water, non-toxic and more volatile than water (generally acetone and/or a lower alcohol), preparing a solution of a suitable surfactant in water (non-solvent for the polymer and the lipid phase), pouring the organic phase into the aqueous phase while stirring the latter phase moderately, which results in the spontaneous formation of an emulsion of nanocapsules, and then evaporating the organic phase and, possibly, some of the aqueous phase, which gives a concentrated suspension of nanocapsules in an aqueous phase.

This preparation process generally involves heating the organic phase and/or the aqueous phase to temperatures of between 35 and 70° C. The dendritic polyesters used in the present invention allow this process to be carried out at room temperature, which constitutes a considerable advantage in particular for heat-sensitive active substances such as retinol.

The surfactant serves primarily to control the size of the nanocapsules. It does this by stabilizing the nanocapsules in the emulsion resulting from pouring the acetone phase into the aqueous phase and preventing them from coalescing.

Any surfactant of hydrophilic nature can be used, whether it is a nonionic, anionic or cationic surfactant. Examples which may be mentioned are sodium lauryl sulphate, quaternary ammonium compounds, sorbitan monoesters which may or may not be polyoxyethylenated, fatty alcohol ethers of polyoxyethylene glycol, condensates of ethylene oxide and of propylene oxide, such as the product Pluronic® F-68 sold by the company BASF, or phospholipids such as lecithin.

The weight ratio of the surfactant to the materials constituting the nanocapsules is advantageously between 0.01 and 0.5 and preferably in the region of 0.2.

It is often desirable or necessary to provide the nanocapsules with a so-called "lamellar" coat. This is a structure organized into one or more lipid leaflet(s) each consisting of a bilayer of amphiphilic molecules which are similar to that of biological membranes. Besides its function of adjusting the size of the nanocapsules, this coat improves the leak-tightness of the nanocapsules with respect to a leakage of the active principle towards other lipid phases of the composition.

The coating agents are surfactants of hydrophobic nature that are soluble in the organic phase used in the present process and that are capable, in the presence of water, of forming the lipid bilayers described above. In the process for encapsulating active principles which is used by the Applicant Company, this coating agent is dissolved in the organic phase (acetone/alcohol) containing the polymer and the lipid phase.

Examples of coating agents which may be mentioned are phospholipids such as lecithin, according to patent application EP-A-447 318, certain polycondensates of ethylene oxide and of propylene oxide, such as the products sold under the name Pluronic® by the company BASF, such as Pluronic 121, or under the name Synperonic® by the company ICI, or certain silicone surfactants, such as those described in documents U.S. Pat. Nos. 5,364,633 and 5,411,744 and used in patent application FR-A-2 742 677, for example those sold by the company Dow Corning under the names DC 5329, DC 7439-146, DC 2-5695 and Q4-3667.

The size of the nanocapsules based on dendritic polymers thus obtained is advantageously between 50 and 800 nm, preferably between 100 and 300 nm.

The nanoencapsulation process of the present invention allows the encapsulation of any kind of lipophilic cosmetic or dermatological active principles.

Examples which may be mentioned are emollients, anti-inflammatory agents, antibacterial agents, antifungal agents, antiviral agents, anti-seborrhoeic agents, anti-acne agents, keratolytic agents, antihistamines, anaesthetics, cicatrizing agents, pigmentation modifiers, sunscreens, free-radical scavengers, moisturizers, vitamins and other similar lipophilic compounds.

According to the present invention, the encapsulated active principle is preferably a lipophilic active principle that is sensitive to the surrounding physicochemical conditions such as the temperature, the pH, light or the presence of oxidizing agents.

Examples of preferred lipophilic active principles which may be mentioned are vitamins such as vitamin A (retinol) or esters thereof, vitamin E or esters thereof, such as tocopheryl acetate, vitamin D or derivatives thereof and vitamin F or derivatives thereof, carotenes such as β-carotene or derivatives thereof such as lykopene, and salicylic acid or derivatives thereof, in particular those described in documents FR-A-2 581 542, EP-A-378 936 and EP-A-570 230, in particular 5-n-octanoylsalicylic acid, 5-n-decanoylsalicylic acid, 5-n-dodecanoylsalicylic acid, 5-n-octylsalicylic acid, 5-n-heptyloxysalicylic acid and 4-n-heptyloxysalicylic acid.

Excellent results have been obtained in particular for the encapsulation of retinol (vitamin $A_1$), which is a molecule that is very sensitive to oxidation at acidic pH, as well for the $C_{1-30}$, more particularly $C_{1-6}$, esters thereof, such as retinyl acetate and retinyl propionate.

A subject of the present invention is also cosmetic and/or dermatological compositions containing, in a physiologically acceptable support, the nanocapsules based on dendritic polymers described above.

The fraction represented by the nanocapsules in the cosmetic and/or dermatological compositions of the present invention is generally between 0.1 and 30% by weight and preferably between 0.5 and 15% by weight relative to the total weight of the composition.

In addition to the nanocapsules and the aqueous phase, the compositions can contain known cosmetic and/or pharmaceutical adjuvants such as fatty substances, petroleum jelly, pH regulators, preserving agents, thickeners, dyes or fragrances.

Needless to say, a person skilled in the art will take care to select this or these optional additional compound(s) and the amount thereof, such that the advantageous properties intrinsically associated with the cosmetic or dermatological composition in accordance with the invention are not, or are not substantially, adversely affected by the addition(s) envisaged.

The compositions according to the invention can be, for example, in the form of a serum, a lotion, an aqueous, aqueous-alcoholic or oily gel, a water-in-oil or oil-in-water emulsion or in the form of aqueous dispersions of lipid vesicles consisting of ionic or nonionic lipids or of a mixture thereof, these vesicles possibly containing an oily phase.

The examples given below, purely for illustrative and non-limiting purposes, will make it possible to gain a better understanding of the invention.

EXAMPLE 1

Preparation of Nanocapsules Based on Dendritic Polyester

The following are dissolved, with stirring and under an inert atmosphere, in a 500 ml amber-glass round-bottomed flask:

- 1 g of dendritic polyester of trimethylolpropane and of dimethylolpropionic acid, sold under the name Boltorn® H40 (TMP core) by the company Perstorp;
- 5 g of triglycerides of caprylic acid and of capric acid (lipid phase) containing 10% retinol, and
- 1 g of a polyethoxylated nonionic surfactant sold under the name Pluronic® L121 by the company BASF, in 200 ml of an acetone/ethanol mixture (85/15). 0.5 g of a nonionic surfactant (triblock polycondensate of ethylene oxide and of propylene oxide, sold under the name Pluronic® F68 by the company BASF) is dissolved in 300 g of water at room temperature in a 1 l amber-glass round-bottomed flask.

The aceto-alcoholic phase is poured into the aqueous phase with moderate stirring.

The acetone and some of the water are then evaporated off in a rotary evaporator, down to a final volume of 100 ml.

This aqueous suspension contains nanocapsules with a mean diameter of 230 nm.

EXAMPLE 2

Preparation of Nanocapsules Based on Dendritic Polyester

The process is performed as described in Example 1, but replacing the dendritic polyester of trimethylolpropane and of dimethylolpropionic acid with an equivalent amount by weight of a dendritic polyester of oxyethylenated pentaerythritol (on average 5 units of ethylene oxide per hydroxyl function), 50% of the terminal hydroxyl functions of which are esterified with a mixture of caprylic ($C_8$) acid and of capric ($C_{10}$) acid, namely the product Boltorn® H30 (esterified) sold by the company Perstorp.

An aqueous suspension of nanocapsules with a mean diameter of 202 nm is obtained.

EXAMPLE 3

Tests of Stability of Retinol Encapsulated in Various Polymers

The stability of retinol enclosed in the nanocapsules based on dendritic polymers (obtained in Example 2) is compared with the stability of this active principle in nanocapsules based on known polymers, namely polycaprolactone and cellulose acetobutyrate, coated with various coating agents.

The nanocapsules containing retinol are stored in closed packaging which is lightproof and gastight, in the form of an aqueous suspension, for one month at 45° C. After this storage period, the loss of active principle (retinol) is evaluated by HPLC assay.

The results obtained are collated in the table below.

| Polymer | Boltorn ® H30 50% esterified with $C_{8/10}$ fatty acids | Polycaprolactone | Cellulose acetobutyrate |
|---|---|---|---|
| Molar mass of the polymer | 4713 | 50,000 | 30,000 |
| Tm of the polymer (in ° C.) | 70–90 | 58–60 | 155–165 |
| Coating agent | Pluronic ® L121* | lecithin | Synperonic ® * | Synperonic ® * |
| Mean diameter of the nanocapsules | 202 nm | 196 nm | 331 nm | 227 nm |
| pH of the composition | 4.75 | 4.2 | 4.5 | 4.9 |
| Loss of active principle after 1 month at 45° C. | 20% | 100% | 41% | 32% |

*Synperonic ® and Pluronic ® are trade names of triblock polycondensates of propylene oxide and of ethylene oxide, which are sold, respectively, by the companies ICI and BASF.

These results show that the use of the dendritic polymers for the preparation of nanocapsules significantly improves the stability to oxidation of the encapsulated retinol, and does so at a pH below 5.

What is claimed is:
1. Nanocapsules comprising
   a lipid core forming or containing a lipophilic active principle, and
   a water-insoluble continuous polymeric envelope, wherein said polymeric envelope comprises at least one dendritic polyester polymer which contains terminal hydroxyl groups.
2. Nanocapsules according to claim 1, wherein the dendritic polyester polymer is a highly branched macromolecule comprising
   a central unit derived from an initiator compound bearing one or more hydroxyl groups (a),
   chain-extending units derived from a chain-extending molecule bearing a carboxyl group (b) and at least two hydroxyl groups (c), each of the hydroxyl groups (a) of the central unit being the starting point of a polycondensation reaction between the hydroxyl groups (a) of the central unit and the carboxyl groups (b) of the chain-extending molecule, and continuing by reaction of the carboxyl groups (b) with the hydroxyl groups (c) of the chain-extending molecule.
3. Nanocapsules according to claim 2, wherein the initiator compound bearing one or more hydroxyl groups, forming the central unit, is selected from the group consisting of
   (a) a monofunctional alcohol,
   (b) an aliphatic diol, a cycloaliphatic diol, an aromatic diol,
   (c) a triol,
   (d) a tetrol,
   (e) a sugar alcohol,
   (f) anhydro-ennea-heptitol, dipentaerythritol,
   (g) an α-alkylglycoside, and
   (h) a polyalkoxy polymer obtained by polyalkoxylation of one of the alcohols (a) to (g), with a molar mass of not more than 8000.
4. Nanocapsules according to claim 3, wherein the initiator compound is selected from the group consisting of ditrimethylolpropane, ditrimethylolethane, dipentaerythritol, pentaerythritol, an alkoxylated pentaerythritol, trimethylolethane, trimethylolpropane, an alkoxylated trimethylolpropane, glycerol, neopentyl glycol, dimethylolpropane and 1,3-dioxane-5,5-dimethanol.
5. Nanocapsules according to claim 2 wherein the chain-extending molecule is selected from the group consisting of monocarboxylic acids comprising at least two hydroxyl groups, and monocarboxylic acids comprising at least two hydroxyl groups, wherein at least one of said hydroxyl groups comprises a hydroxyalkyl substituent.

6. Nanocapsules according to claim 5, wherein the chain-extending molecule is selected from the group consisting of dimethylolpropionic acid, α,α-bis(hydroxymethyl)butyric acid, α,α,α-tris(hydroxymethyl)acetic acid, α,α-bis (hydroxymethyl)valeric acid, α,α-bis-(hydroxy)propionic acid and 3,5-dihydroxybenzoic acid.

7. Nanocapsules according to claim 2, wherein the initiator compound is selected from the group consisting of trimethylolpropane, pentaerythritol and a polyethoxylated pentaerythritol, and the chain-extending molecule is dimethylolpropionic acid.

8. Nanocapsules according to claim 2, wherein at least a portion of the terminal hydroxyl groups of the dendritic polyester polymer bear substituents derived from at least one chain-terminating agent.

9. Nanocapsules according to claim 8, wherein the chain-terminating agent is selected from the group consisting of i) saturated or unsaturated, aliphatic or cycloaliphatic monocarboxylic acids (or anhydrides), ii) saturated or unsaturated fatty acids, iii) aromatic monocarboxylic acids, iv) diisocyanate monomers or oligomers or addition products thereof, v) epihalohydrins, vi) glycidyl esters of a monocarboxylic acid or of a $C_{1-24}$ fatty acid, vii) glycidyl ethers of $C_{1-24}$ monovalent alcohols, viii) addition products derived from a saturated or unsaturated, aliphatic or cycloaliphatic mono-, di- or polycarboxylic acid, or from the corresponding anhydrides, ix) addition products derived from an aromatic mono-, di- or polycarboxylic acid or from the corresponding anhydrides, x) epoxides of an unsaturated $C_{3-24}$ monocarboxylic acid or of a corresponding triglyceride, xi) saturated or unsaturated, aliphatic or cycloaliphatic monofunctional alcohols, xii) aromatic monofunctional alcohols, xiii) addition products derived from a saturated or unsaturated, aliphatic or cycloaliphatic mono-, di- or polyfunctional alcohol, and xiv) addition products derived from an aromatic mono-, di- or polyfunctional alcohol.

10. Nanocapsules according to claim 9, wherein the chain-terminating agent is selected from the group consisting of lauric acid, linseed fatty acids, soybean fatty acids, tallow fatty acids, dehydrogenated castor oil fatty acids, crotonic acid, capric acid, caprylic acid, acrylic acid, methacrylic acid, benzoic acid, para-tert-butylbenzoic acid, abietic acid, sorbinic acid, 1-chloro-2,3-epoxypropane, 1,4-dichloro-2,3-epoxybutane, epoxidized soybean fatty acids, trimethylolpropane diallyl ether maleate, 5-methyl-1,3-dioxane-5-methanol, 5-ethyl-1,3-dioxane-5-methanol, trimethylolpropane diallyl ether, pentaerythrityl triallyl ether, pentaerythrityl triacrylate, triethoxylated pentaerythrityl triacrylate, toluene 2,4-diisocyanate, toluene 2,6-diisocyanate, hexamethylene diisocyanate and isophorone diisocyanate.

11. Nanocapsules according to claim 10, in which the chain-terminating agent is a mixture of capric acid and caprylic acid.

12. Nanocapsules according to claim 8, wherein the fraction of terminal hydroxyl groups bearing a chain-terminating unit is between 1 and 90 mol % relative to the total number of terminal hydroxyl groups.

13. Nanocapsules according to claim 1, wherein said nanocapsules are surrounded by a lamellar coat with a structure organized into one or more leaflet(s) each comprising a bilayer of an amphiphilic coating agent.

14. Nanocapsules according to claim 13, wherein said coating agent is selected from the group consisting of phospholipids, polycondensates of propylene oxide and of ethylene oxide, and silicone surfactants, which are capable of forming lamellar structures.

15. Nanocapsules according to claim 14, wherein said nanocapsules have a mean size of between 50 nm and 800 nm.

16. Nanocapsules according to claim 1, wherein the encapsulated lipophilic active principles are selected from the group consisting of emollients, anti-inflammatory agents, antibacterial agents, antifungal agents, antiviral agents, antiseborrhoeic agents, anti-acne agents, keratolytic agents, antihistamines, anaesthetics, cicatrizing agents, pigmentation modifiers, sunscreens, free-radical scavengers, moisturizers and vitamins.

17. Nanocapsules according to claim 16, wherein the encapsulated lipophilic active principle is selected from active principles that are sensitive to the surrounding physicochemical conditions or the presence of oxidizing agents.

18. Nanocapsules according to claim 17, wherein the lipophilic active principle is selected from the group consisting of vitamins, esters of vitamins, derivatives of vitamins, carotenes derivatives of carotenes, salicylic acid and derivatives of salicylic acid.

19. Nanocapsules according to claim 18, wherein the lipophilic active principle is retinol or a $C_{1-30}$ ester thereof.

20. A cosmetic and/or dermatological composition, comprising, in a physiologically acceptable support, the nanocapsules of claim 1.

21. A cosmetic and/or dermatological composition according to claim 20, wherein the fraction of nanocapsules is between 0.1 and 30% by weight relative to the total weight of the composition.

22. A cosmetic and/or dermatological composition according to claim 20, further comprising cosmetic and/or pharmaceutical adjuvants.

23. A cosmetic and/or dermatological composition according to claim 20, in the form of a serum, a lotion, an aqueous, aqueous-alcoholic or oily gel, a water-in-oil or oil-in-water emulsion or in the form of an aqueous dispersion of lipid vesicles comprising ionic or nonionic lipids or of a mixture thereof, the vesicles optionally containing an oily phase.

24. A process for preparing the nanocapsules according to claim 1, said process comprising:

dissolving a polymer, a lipid phase forming or containing an active principle and optionally a coating agent, in a water-miscible organic solvent, preparing an aqueous solution of a surfactant, pouring the organic phase into the aqueous phase while stirring the latter phase moderately, and then evaporating the organic phase and, optionally, some of the aqueous phase, said polymer being a dendritic polyester polymer.

25. Nanocapsules according to claim 15, wherein said mean size is between 100 and 300 nm.

26. Nanocapsules according to claim 18, wherein said lipophilic active principle is selected from the group consisting of vitamin A, vitamin E, vitamin D, vitamin F, a vitamin A derivative, a vitamin E derivative, a vitamin D derivative, a vitamin F derivative, β-carotene, lykopene, 5-n-octanoylsalicylic acid, 5-n-decanoylsalicylic acid, 5-n-dodecanoylsalicylic acid, 5-n-octylsalicylic acid, 5-n-heptyloxysalicylic acid and 4-n-heptyloxysalicylic acid.

* * * * *